(12) United States Patent
Yada et al.

(10) Patent No.: US 7,244,863 B2
(45) Date of Patent: Jul. 17, 2007

(54) PROCESS FOR PRODUCING (METH)ACRYLIC ACID COMPOUND

(75) Inventors: Shuhei Yada, Mie (JP); Yasushi Ogawa, Mie (JP); Yoshiro Suzuki, Mie (JP); Hirochika Hosaka, Mie (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 10/849,170

(22) Filed: May 20, 2004

(65) Prior Publication Data
US 2005/0054874 A1    Mar. 10, 2005

Related U.S. Application Data

(63) Continuation of application No. PCT/JP02/11959, filed on Nov. 15, 2002.

(30) Foreign Application Priority Data
Nov. 20, 2001   (JP) ............................ P.2001-354043

(51) Int. Cl.
*C07C 51/42* (2006.01)
(52) U.S. Cl. .................................... 562/600
(58) Field of Classification Search ................ None
See application file for complete search history.

(56) References Cited

U.S. PATENT DOCUMENTS

| 4,317,926 A | 3/1982 | Sato et al. |
| 5,734,075 A | 3/1998 | Fauconet et al. |
| 6,448,438 B1 | 9/2002 | Yada et al. |
| 2005/0054874 A1 | 3/2005 | Yada et al. |

FOREIGN PATENT DOCUMENTS

| EP | 0 887 334 A1 | 12/1998 |
| EP | 1 043 302 A2 | 10/2000 |
| JP | 54-98718 | 8/1979 |
| JP | 8 183756 | 7/1996 |

OTHER PUBLICATIONS

U.S. Appl. No. 10/834,075, filed Apr. 29, 2004, Yada, et al.
U.S. Appl. No. 10/834,177, filed May 3, 2004, Yada, et al.
U.S. Appl. No. 10/853,199, filed May 26, 2004, Yada, et al.
U.S. Appl. No. 10/854,704, filed May 27, 2004, Yada, et al.
U.S. Appl. No. 10/864,498, filed Jun. 10, 2004, Yada, et al.
U.S. Appl. No. 11/434,067, filed May 16, 2006, Yada, et al.
U.S. Appl. No. 11/226,360, filed Sep. 15, 2005, Yada, et al.
U.S. Appl. No. 10/898,341, filed Jul. 26, 2004, Yada, et al.
U.S. Appl. No. 11/103,617, filed Apr. 12, 2005, Yada, et al.
U.S. Appl. No. 11/103,622, filed Apr. 12, 2005, Yada, et al.

*Primary Examiner*—Paul A. Zucker
(74) *Attorney, Agent, or Firm*—Oblon, Spivak, McClelland, Maier & Neustadt, P.C.

(57) ABSTRACT

The invention provides a process for producing and/or purifying acrylic acid or methacrylic acid or an ester of any of these, wherein mixtures of high-boiling heavy ingredients (high-boiling matter mixtures) discharged from individual step units are classified by the content therein of (meth)acrylic acid and/or of the dimer thereof and handled. According to the invention, even when high-boiling matters which have been discharged from distillation columns, high-boiling-matter cracking reactors, and the like in a plant for producing (meth)acrylic acid and/or an ester thereof and are alike in liquid nature are mixed with each other in the same tank, no polymer precipitation occurs. The handling and storage thereof are hence easy. Consequently, tanks can be united into one, and the process is extremely advantageous in reducing the construction cost and the area necessary for equipment.

8 Claims, 5 Drawing Sheets

PROCESS FOR PRODUCING (METH)ACRYLIC ACID COMPOUND

This application is a continuation of international application PCT/JP02/11959, filed Nov. 15, 2002.

TECHNICAL FIELD

The present invention relates to a process for producing acrylic acid or methacrylic acid or an ester of any of these (hereinafter referred to as "(meth)acrylic acid compound"). More particularly, the invention relates to a process for producing and/or purifying a (meth)acrylic acid compound wherein high-boiling matters discharged from individual step units are easily handled and efficiently stored.

BACKGROUND ART

In a process for producing acrylic acid or methacrylic acid (hereinafter referred to as (meth)acrylic acid) by catalytic vapor-phase oxidation and in a process for producing a (meth)acrylic ester by direct esterification, various high-boiling matters generate in individual step units such as a dehydration column, distillation column, acetic acid separation column, high-boiling-matter cracking reactor (high-boiling-matter cracking column), and the like. In general, these high-boiling matters are temporarily stored in tanks and thereafter subjected to a treatment such as recovery treatment, incineration disposal, or landfill disposal. Some kinds of high-boiling matters are stored in tanks via a high-boiling-matter cracking reactor. For storage, tanks disposed respectively for separate production processes have been used because the high-boiling matters are yielded from a variety of sources and have properties characteristic of the individual processes.

Such a storage method heretofore in use is intended to avoid a trouble that when high-boiling matters generating in individual processes are mixed, then the polymerization inhibitor, by-product polymers, and the like contained therein precipitate. This is because the polymers precipitated adhere as a tacky ingredient to the inside of an apparatus to arouse troubles. This necessitates separate tanks for high-boiling matters in plant construction. There has hence been a problem that the construction cost is high and the area necessary for tank installation is large.

DISCLOSURE OF THE INVENTION

The present inventors made intensive investigations in order to eliminate those problems. As a result, it has been found that when high-boiling matters discharged from individual processes are classified by composition concerning specific ingredients and the high-boiling matters alike in composition are mixed together, then tanks can be united and operated without causing any change in liquid state. The invention has been thus completed.

Namely, an essential point of the invention resides in a process for producing a (meth)acrylic acid compound which is a process for producing and/or purifying acrylic acid or methacrylic acid or an ester of these, characterized in that mixtures of high-boiling heavy ingredients (hereinafter referred to as "high-boiling matter ingredients") discharged from individual step units are classified by the content therein of (meth)acrylic acid and/or the dimer thereof and handled.

Figure 1:
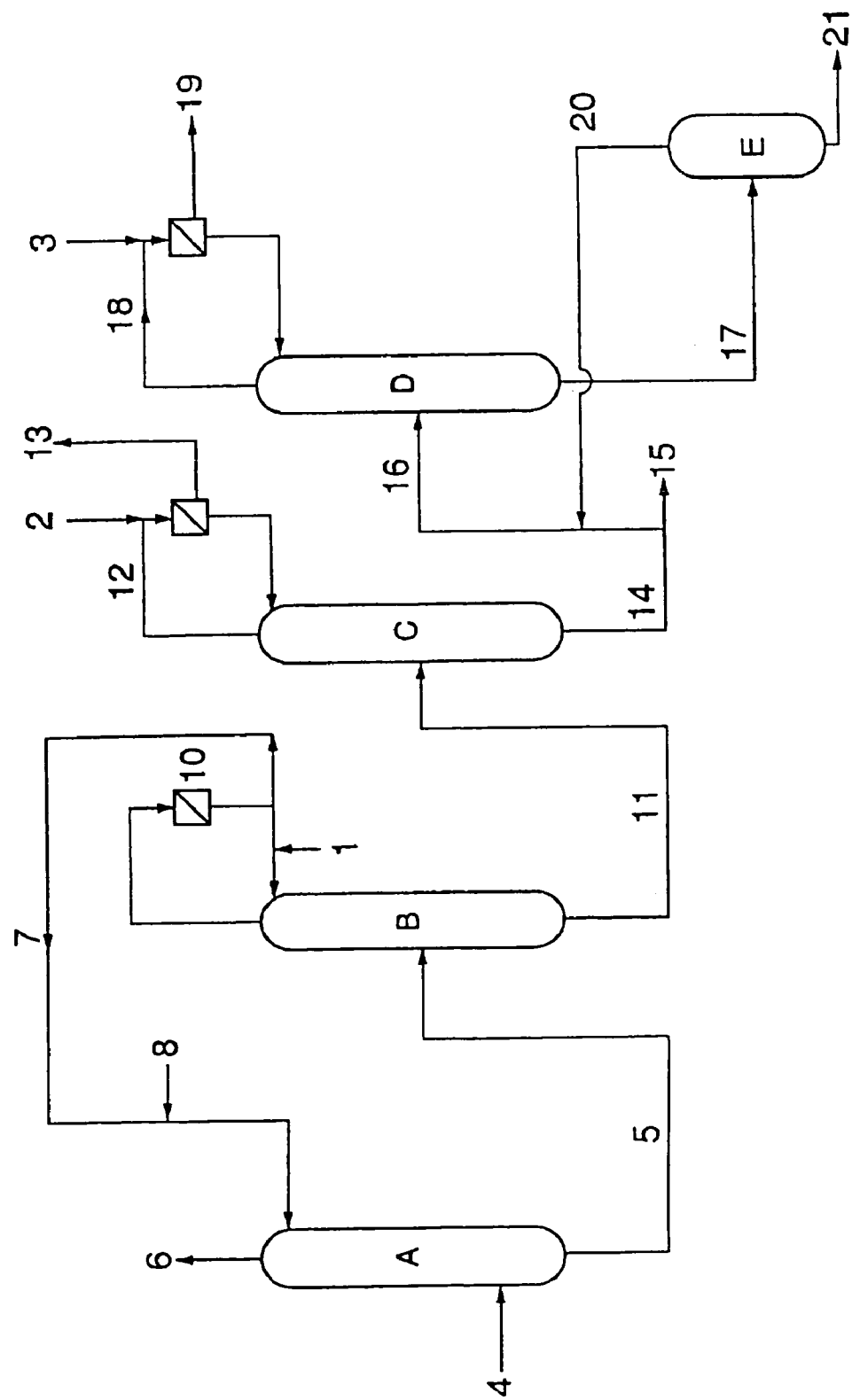
FIG. 1 is a flow diagram of one example of processes for producing acrylic acid from propylene as a starting material.

In the figures, sings and numerals have the following meanings.
A denotes an acrylic acid collection column,
B a dehydration column,
C a low-boiling separation column (acetic acid separation column),
D a high-boiling separation column (acrylic acid purification column),
E a high-boiling cracking reactor,
F a distillation column into which the dehydration column B and low-boiling separation column (acetic acid separation column) C have been united,
G a stripping column,
H a high-boiling removal column,
K a solvent purification column,
L an esterification reactor,
M an acrylic acid separation column,
N a high-boiling cracking reactor,
Q an alcohol extraction column,
P an alcohol recovery column,
R a low-boiling separation column,
S an ester purification column, and
T a high-boiling-matter storage tank.

BEST MODE FOR CARRYING OUT THE INVENTION

The process of the invention can be applied to handling of high-boiling heavy ingredients (high-boiling matters) obtained in the distillation of acrylic acid, methacrylic acid, or esters thereof, i.e., acrylic monomers. For example, it can be applied to a process for producing acrylic acid by subjecting propane to vapor-phase oxidation using an Mo—V—Te composite oxide catalyst, Mo—V—Sb composite oxide catalyst, or the like or a process for producing acrylic acid or methacrylic acid by subjecting propylene or isobutylene to vapor-phase catalytic oxidation in the presence of an Mo—Bi composite oxide catalyst to yield acrolein or methacrolein and further subjecting it to vapor-phase catalytic oxidation in the presence of an Mo—V composite oxide catalyst. This process may be one wherein the preceding reaction in which propylene is oxidized to mainly yield acrolein and the succeeding reaction in which the acrolein is oxidized to mainly yield acrylic acid are separately conducted in respective reactors, or may be one wherein the catalyst for the preceding reaction and the catalyst for the succeeding reaction are simultaneously packed into one reactor to conduct the reactions. Furthermore, the invention can be applied to a process in which acrylic acid or methacrylic acid is used as a starting material to produce an ester thereof.

Examples of acrylic esters include methyl acrylate, ethyl acrylate, butyl acrylate, isobutyl acrylate, tertiary butyl acrylate, 2-ethylhexyl acrylate, 2-hydroxyethyl acrylate, 2-hydroxypropyl acrylate, methoxyethyl acrylate, and the like. Examples of methacrylic esters include similar compounds.

The unpurified acrylic monomers obtained by these production processes generally contain high-boiling impurities such as the dimers and trimers of the acrylic monomers, esters thereof, maleic anhydride, benzaldehyde, β-hydroxypropionic acid, β-hydroxypropionic esters, β-alkoxypropionic acids, and β-alkoxypropionic esters.

When an acrylic monomer containing such high-boiling impurities is distilled, the (meth)acrylic acid compound is obtained as a distillate ingredient from the distillation column, while a high-boiling matter is obtained as bottom ingredients. High-boiling matters further include ones which have been concentrated, yielded, or separated in steps other than distillation columns, e.g., high-boiling cracking reactors (cracking residues, concentrates, and the like). The invention is applied to handling, such as storage, transportation, and keeping, of such high-boiling matters.

Next, processes for producing acrylic acid and an acrylic ester will be explained as examples using drawings.

FIG. 1 is a flow diagram of one example of processes for producing acrylic acid from propylene as a starting material. The signs and numerals in the figure are as follows.

A: acrylic acid collection column
B: dehydration column
C: low-boiling separation column (acetic acid separation column)
D: high-boiling separation column (acrylic acid purification column)
E: high-boiling cracking reactor
1–3: polymerization inhibitor supply line
4: oxidation reaction gas containing acrylic acid
5: aqueous acrylic acid solution line
11: crude acrylic acid line
15: acrylic acid withdrawal line
19: high-purity acrylic acid withdrawal line
21: high-boiling matter withdrawal line An acrylic-acid-containing gas 4 obtained by the catalytic vapor-phase oxidation of propane, propylene, and/or acrolein with a gas comprising molecular oxygen is introduced into an acrylic acid collection column A through a line and brought into contact with water to obtain an aqueous acrylic acid solution.

Subsequently, the aqueous acrylic acid solution is supplied to a dehydration column B. An entrainer is supplied to the dehydration column. An azeotropic mixture comprising water and the entrainer is obtained through the column top by distillation, while acrylic acid containing acetic acid is obtained from the bottom of the column. The azeotropic mixture which comprises water and the entrainer and has been obtained through the column top by distillation is introduced into a storage vessel 10, wherein the mixture is separated into an organic phase consisting mainly of the entrainer and an aqueous phase consisting mainly of water. The organic phase is circulated to the dehydration column B. On the other hand, the aqueous phase is circulated to the acrylic acid collection column A through a line 7 and used as collecting water to be contacted with the acrylic-acid-containing gas. Thus, the two phases can be effectively utilized. Water is supplied according to need through a line 8. For the purpose of recovering the entrainer present in the process liquid in the line 7, the aqueous phase may be circulated through an entrainer recovery column (not shown) to the acrylic acid collection column A.

The crude acrylic acid withdrawn from the bottom of the dehydration column B through a line 11 is introduced into a low-boiling separation column (acetic acid separation column) C in order to remove the acetic acid remaining therein. The acetic acid here is separated and removed through the column top and lines 12 and 13. There are cases where the acetic acid in the line 13 is partly or wholly returned to the process because it contains acrylic acid. On the other hand, acrylic acid containing substantially no acetic acid is obtained from the bottom of the column through a line 14. Since this acrylic acid has a considerably high purity, it can be used by itself as a starting material for an acrylic ester. In some cases, this acid is shipped as a product through a line 15. In order to obtain acrylic acid having a higher purity, the acrylic acid obtained above is introduced into a high-boiling separation column (acrylic acid purification column) D through a line 16 and high-boiling substances are separated and removed through a line 17. Thus, high-purity acrylic acid can be obtained through lines 18 and 19. The high-boiling matter in the line 17 is introduced into a high-boiling cracking reactor E, and part thereof is recovered as acrylic acid and sent to the process through a line 20. A high-boiling matter is separated and removed through a line 21 and stored and kept in a tank (not shown).

Figure 2:
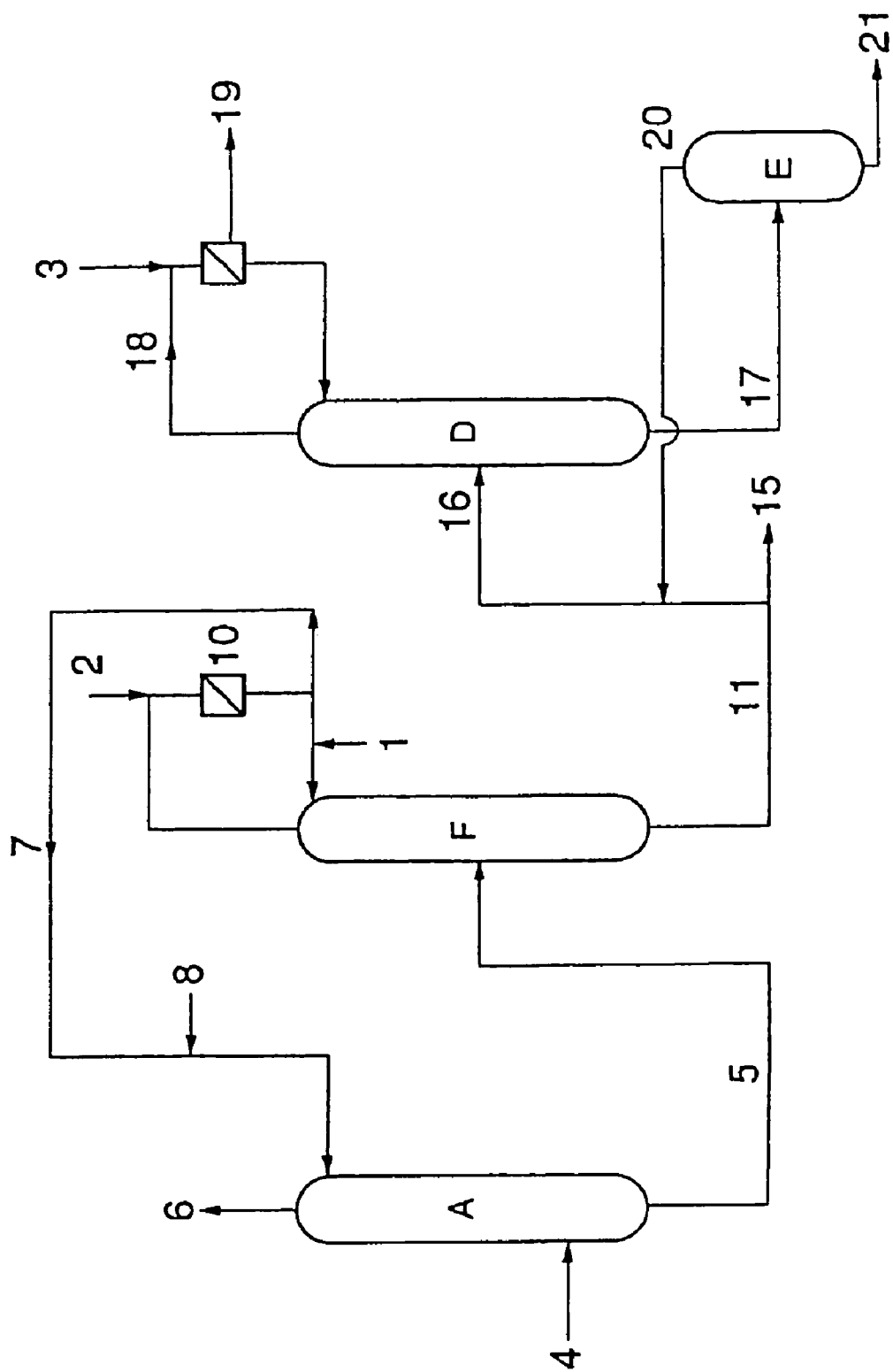
FIG. 2 is a flow diagram of another example of processes for producing acrylic acid.

FIG. 2 is a flow diagram of another example of processes for producing acrylic acid.

This is a process in which the dehydration column B and low-boiling separation column (acetic acid separation column) C in FIG. 1 have been united into one column, i.e., a distillation column F. The flows of substances are basically the same as in FIG. 1.

Figure 3:
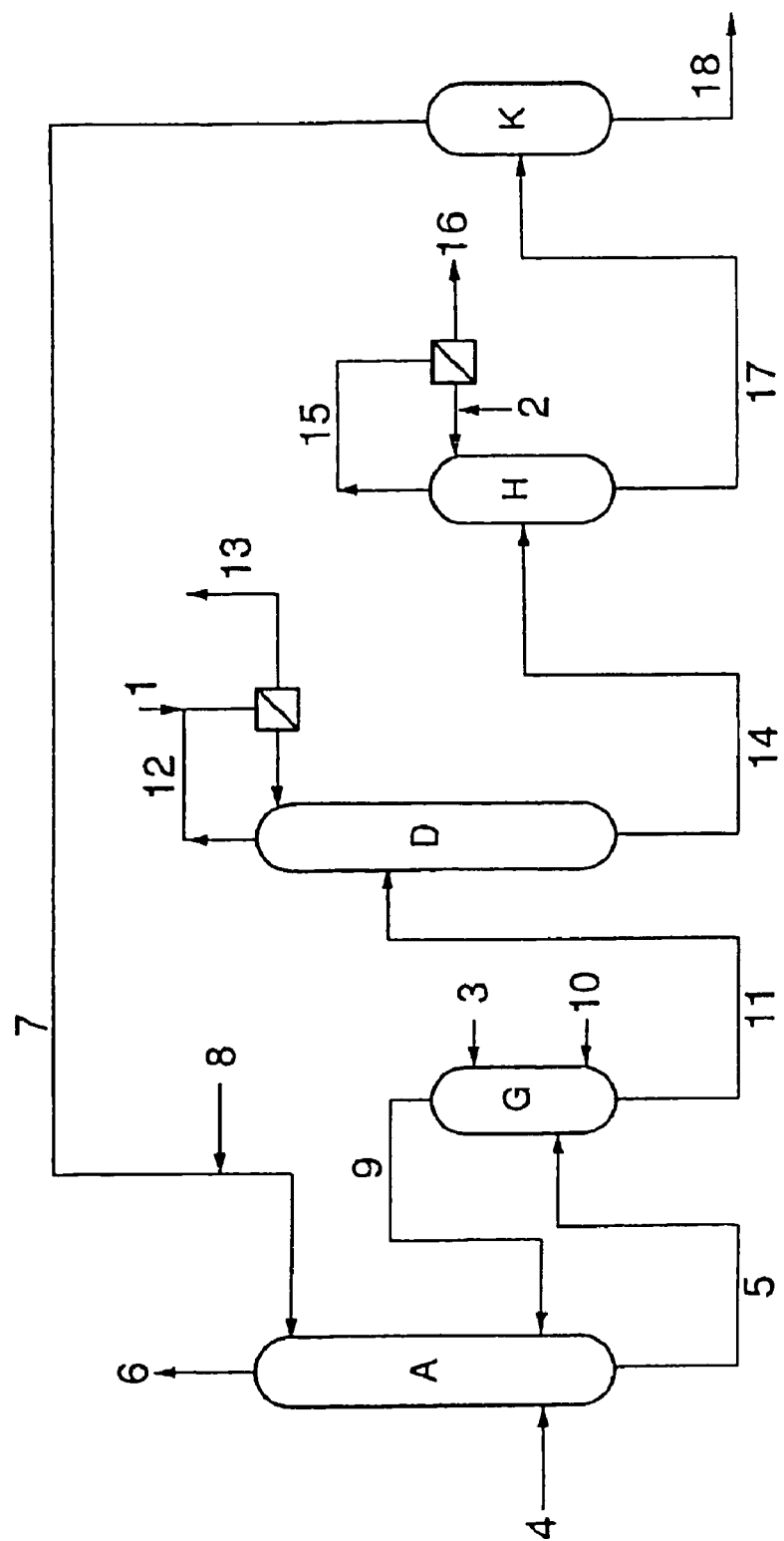
FIG. 3 is a flow diagram of still another example of processes for producing acrylic acid.

FIG. 3 is a flow diagram of still another example of processes for producing acrylic acid.

A: acrylic acid collection column
G: stripping column
D: high-boiling separation column (acrylic acid purification column)
H: high-boiling removal column
K: solvent purification column
1–3: polymerization inhibitor supply line
4: oxidation reaction gas containing acrylic acid
5: acrylic-acid-containing solution line
11: crude acrylic acid line
13: high-purity acrylic acid withdrawal line An acrylic-acid-containing gas 4 obtained by the catalytic vapor-phase oxidation of propane, propylene, and/or acrolein with a gas comprising molecular oxygen is introduced into an acrylic acid collection column A through a line and brought into contact with a solvent to obtain an acrylic-acid-containing solution.

Subsequently, the acrylic-acid-containing solution is supplied to a stripping column G. A gas (e.g., the gas in a line 6 discharged from the top of the acrylic acid collection column A or a gas obtained by oxidizing and removing organic substances in the gas in the line 6) is supplied to the stripping column G through a line 10. Water and acetic acid are obtained through the column top by distillation, while acrylic acid containing the solvent is obtained through the bottom of the column. The water and acetic acid recovered by distillation through the top of the stripping column G are introduced into the acrylic acid collection column A. The water and acetic acid are finally discharged through the top of the acrylic acid collection column A. In order to obtain high-purity acrylic acid, the solvent-containing acrylic acid is introduced from the bottom of the stripping column G into a high-boiling separation column (acrylic acid purification column) D through a line 11 and high-boiling substances are separated and removed through a line 14. Thus, high-purity acrylic acid can be obtained through a line 13. The high-boiling substances in the line 14 specifically include maleic anhydride, benzaldehyde, and the like. These high-boiling substances are introduced into a high-boiling removal column H and discharged through a line 16. The solvent is introduced from the bottom of the column to a solvent purification column K through a line 17. Although the solvent recovered is returned through the column top and a line 7 to the acrylic acid collection column A, part or most of the solvent in the line 17 may be directly returned to the acrylic acid collection column A through a piping (not shown) including the line 7. Higher-boiling substances are separated and removed through the bottom of the column and a line 18, and stored/kept in a tank (not shown).

Figure 4:
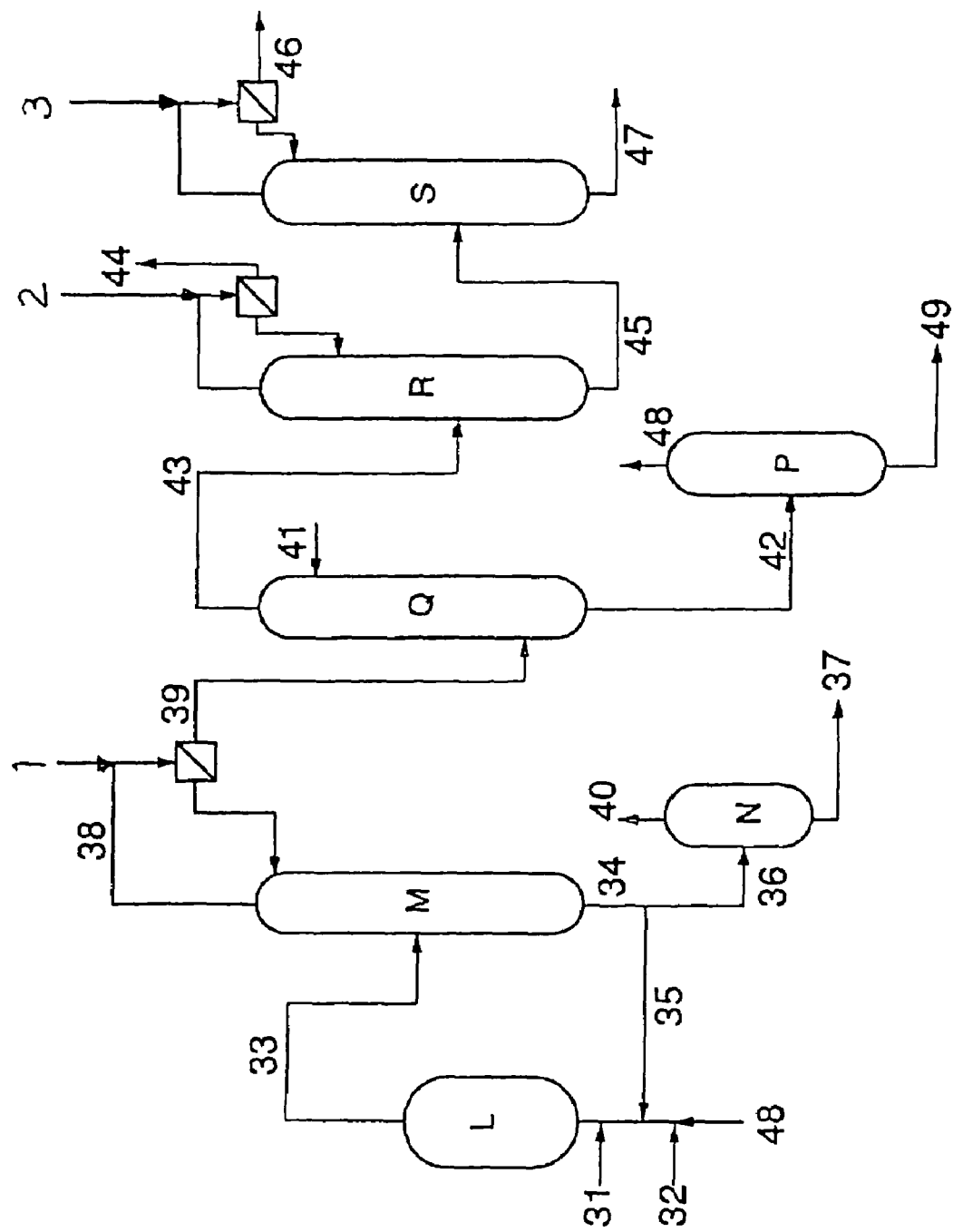
FIG. 4 is a flow diagram of an example of processes for producing an acrylic ester.

FIG. 4 is a flow diagram of an example of processes for producing an acrylic ester. The signs and numerals in the figure are as follows.

L: esterification reactor
M: acrylic acid separation column
N: high-boiling cracking reactor
Q: alcohol extraction column
P: alcohol recovery column
R: low-boiling separation column
S: ester purification column
1–3: polymerization inhibitor supply line
31: acrylic acid feed line
32: alcohol feed line
33: esterification reaction mixture
35: circulating acrylic acid
37: high-boiling impurity withdrawal line
39: crude acrylic ester withdrawal line
41: water supply line
42: line for recovered alcoholic water
46: acrylic ester product withdrawal line Acrylic acid, an alcohol, circulating acrylic acid, and a circulating alcohol are fed to an esterification reactor L through a line 31, line 32, line 35, and line 48, respectively. The esterification reactor L is packed with a catalyst such as a strongly acidic ion-exchange resin. An esterification reaction mixture comprising the ester yielded, unreacted acrylic acid, unreacted alcohol, and water yielded is withdrawn through a line 33 and supplied to an acrylic acid separation column M. Bottoms containing substantially all of the unreacted acrylic acid are withdrawn from the acrylic acid separation column M through a line 34, and supplied as a circulating liquid to the esterification reactor L through the line 35.

Part of the bottoms is supplied to a high-boiling cracking reactor N through a line 36, and a valuable substance obtained through cracking is circulated to the process through a line 40. That part in the process to which the valuable substance is circulated varies depending on process conditions. High-boiling impurities including polymers are removed from the system through a line 37 and stored/kept in a tank (not shown). Furthermore, the ester yielded, unreacted alcohol, and water yielded are obtained as a distillate from the top of the acrylic acid separation column M through a line 38. Part of the distillate is circulated as a reflux to the acrylic acid separation column M, while the remainder is supplied to an extraction column Q through a line 39.

Water for alcohol extraction is supplied through a line 41. The alcohol-containing water recovered through a line 42 is supplied to an alcohol recovery column P. The alcohol recovered is circulated to the esterification reactor through a line 48.

The crude acrylic ester is supplied to a low-boiling separation column R through a line 43. Low-boiling substances including the acrylic ester are withdrawn through a line 44 and circulated to a part in the process. That part in the process to which the low-boiling substances are circulated varies depending on process conditions. The crude acrylic ester from which low-boiling substances have been removed is supplied to an acrylic ester product purification column S through a line 45. The acrylic ester having a high purity is obtained from the column top through a line 46. A liquid containing high-boiling substances in a small amount is withdrawn from the bottom of the column through a line 47 and circulated to a part in the process, because it usually contains acrylic acid in a large amount. That part in the process to which the liquid is circulated varies depending on process conditions.

High-boiling matters to which the invention is applied include all which contain all the high-boiling impurity ingredients discharged from individual step units for separating, concentrating, recovering, and purifying a (meth) acrylic acid compound, as shown above as examples. Typical examples thereof are the bottoms discharged through the line 21 shown in FIG. 1 and FIG. 2, line 16 and line 18 shown in FIG. 3, and line 37 shown in FIG. 4.

Such high-boiling matters are obtained as bottom ingredients from a distillation column, bottom ingredients from a high-boiling-matter cracking column, cracking residues from a high-boiling cracking reactor, and the like. The distillation column is not particularly limited in type, plate shape, packing shape, etc. Furthermore, polymerization inhibitors can be used without particular limitations in order to prevent the (meth)acrylic acid compound from polymerizing during distillation or in an operation after distillation. These polymerization inhibitors also may constitute part of the high-boiling matters. The high-boiling cracking reactor also is not particularly limited in shape, type, etc., and use can be made, for example, of any of a column type reactor, tank type reactor, and the like.

The high-boiling matters to be handled in the invention will be described in greater detail. The compositions thereof comprise (meth)acrylic acid, a (meth)acrylic ester, products of radical polymerization of (meth)acrylic acid compounds (frequently referred to simply as polymers), oligomers such as the dimer, trimer, and tetramer which are products of the Michael addition of (meth)acrylic acid, acrylic acid dimer esters, acrylic acid trimer esters, acrylic acid tetramer esters, polymerization inhibitors, maleic acid, benzaldehyde, furfural, alkoxypropionic acids, alkoxypropionic esters, alcohols (e.g., methanol, ethanol, normal butanol, isobutanol, 2-ethylhexyl alcohol, and the like), products of the Michael addition of polymers with (meth)acrylic acid, and the like.

Incidentally, the structural formulae of the dimer and trimer which are products of the Michael addition of acrylic acid are as follows.

Dimer of acrylic acid: $H_2C=CH-C(=O)-O-CH_2-CH_2-C(=O)-OH$

Trimer of acrylic acid: $H_2C=CH-C(=O)-O-CH_2-CH_2-C(=O)-O-CH_2-CH_2-C(=O)-OH$

There are cases where an aldehyde present in a trace amount, such as benzaldehyde or furfural, is reacted with an aldehyde remover (e.g., a hydrazine compound or the like) in producing high-purity (meth)acrylic acid to convert it into a heavy-boiling substance and discharged in this form. There are cases where this substance also is one ingredient contained in a high-boiling matter. Consequently, the high-boiling matters discharged in a process for producing high-purity (meth)acrylic acid can be handled in the invention in the same manner as for the high-boiling matters discharged in a process for crude acrylic acid, as described above.

High-boiling matters to be handled in the invention are not equal in composition depending on how the high-boiling matters have generated. Examples thereof include a high-boiling matter in a (meth)acrylic acid production process which comprises from 5 to 30% by weight (meth)acrylic acid, from 5 to 90% by weight (meth)acrylic acid dimer, from 5 to 50% by weight polymeric ingredients and others, and up to 1% by weight water. Examples thereof further include a high-boiling matter in a (meth)acrylic ester production process which comprises from 5 to 40% by weight (meth)acrylic ester, from 0.1 to 10% by weight (meth)acrylic acid, from 5 to 60% by weight polymeric ingredients and others, and up to 1% by weight water.

The feature of the invention resides in that high-boiling matters are classified by the content of (meth)acrylic acid and/or its dimer in the composition and handled. High-boiling matters in which the content of (meth)acrylic acid and/or its dimer is high, in particular, high-boiling matters in which the total content of these is 10% by weight or higher, especially 20% by weight or higher, are highly hydrophilic and have the high ability to dissolve polymers therein. Consequently, even when high-boiling matters in each of which the total content of (meth)acrylic acid and its dimer is 10% by weight or higher are mixed with each other, neither a change in liquid state nor polymer precipitation occurs.

On the other hand, high-boiling matters in which the content of (meth)acrylic acid and/or its dimer is low, in particular, high-boiling matters in which the total content of these is lower than 10% by weight, especially lower than 8% by weight, are highly hydrophobic. Such high-boiling matters are highly hydrophobic and contain a considerably large amount of polymeric ingredients dissolved therein. Consequently, even when high-boiling matters in which the total content of (meth)acrylic acid and its dimer is lower than 10% by weight are mixed with each other, neither a change in liquid state nor polymer precipitation occurs.

However, when a hydrophilic high-boiling matter in which the content of (meth)acrylic acid and/or its dimer is high is mixed with a hydrophobic high-boiling matter in which the content thereof is low, then polymer precipitation occurs regardless of polymer content, because these high-boiling matters differ in liquid nature.

The term "content of (meth)acrylic acid and/or its dimer" in the invention has the following meaning. When the high-boiling matter contains any one of these ingredients, the term means the content of this ingredient. When the high-boiling matter contains two or more of these ingredients, that term means the content of all of the ingredients.

High-boiling matters which are alike in liquid nature can be mixed with each other regardless of mixing ratio, i.e., in any proportion, and polymer precipitation can be avoided in any case. Operations for mixing also are not particularly limited. For example, various high-boiling matters obtained as bottoms in distillation columns, cracking products or cracking residues in high-boiling cracking reactors, and the like are classified by the content of (meth)acrylic acid and/or its dimer. Thereafter, the high-boiling matters which are alike in liquid nature can be mixed with each other in a piping line or directly introduced into a tank and stored. In some cases, the high-boiling matters can be mixed by means of a small reserve tank for mixing.

Figure 5:
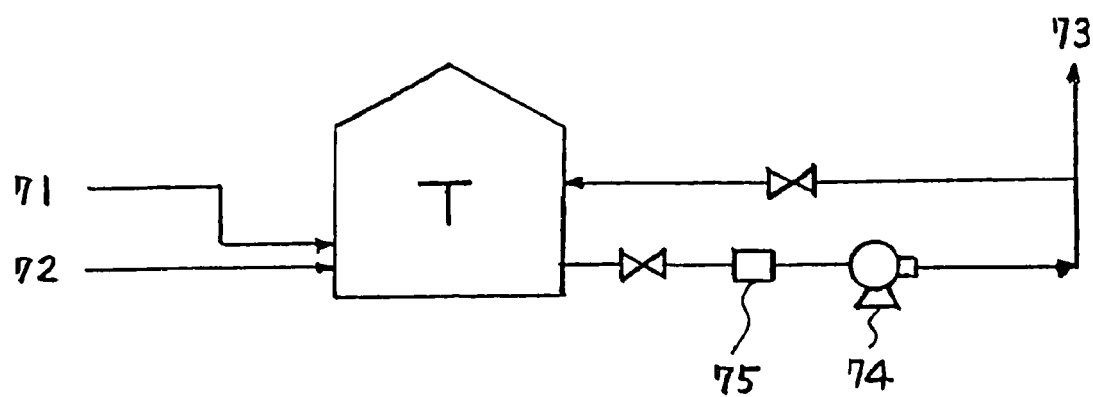
FIG. 5 is an example of a high-boiling-matter mixing tank and apparatus attached thereto.

As shown in FIG. 5, an external circulation line may be disposed for the purpose of heightening the degree of mixing of the high-boiling matters in a tank. It is preferred to dispose a strainer in the circulation line to thereby remove solid ingredients present in a trace amount, such as polymers. In FIG. 5, 71 and 72 denote a high-boiling-matter introduction line, 73 a high-boiling-matter discharge line, 74 a circulating pump, and 75 a strainer.

As described above, high-boiling matters alike in liquid nature can be mixed with each other at will in any desired proportion because the mixing does not result in polymer precipitation. Furthermore, since hydrophilic high-boiling matters in which the content of (meth)acrylic acid and/or its dimer is 10% by weight or higher are hydrophilic in themselves, no polymer precipitation occurs even when they are mixed with valuable-containing various wastewaters, aqueous acetic acid solutions, or the like generating in the process. In this case, the mixing has the effect of lowering the viscosity of the hydrophilic high-boiling matters to facilitate transportation to tanks or cleaning. Incidentally, in the case of hydrophobic high-boiling matters in which the content of (meth)acrylic acid and/or its dimer is lower than 10% by weight, even a small amount of water promotes polymer precipitation. It is therefore preferred to keep the content thereof in these high-boiling matters at 2% by weight or lower, especially 1% by weight or lower.

EXAMPLES

The invention will be explained below in more detail by means of Examples, but the invention should not be construed as being limited to the following Examples unless the invention departs from the spirit thereof. Incidentally, analysis for acrylic acid dimer is as follows.

Acrylic acid was caused to yield a dimer by heating. A calibration curve in gas chromatography for acrylic acid dimer purified by distillation under high vacuum (purity, ≧95% by weight) was drawn beforehand, and the amount of the dimer in a sample was determined based on the calibration curve. As the apparatus and column were used GC14A, manufactured by Shimadzu Corp., and FFAP-10, manufactured by Tokyo Kasei, respectively.

Example 1

A high-boiling matter 1 having the following composition was obtained from a high-boiling cracking reactor in an acrylic acid plant.

| | |
|---|---|
| Acrylic acid; | 8 wt % |
| Acrylic acid dimmer; | 72 wt % |
| Maleic acid; | 8 wt % |
| Others (polymers, polymerization inhibitor, etc.); | 12 wt % |
| Water; | ≦0.1 wt % |

Likewise, a high-boiling matter 2 having the following composition was obtained from a high-boiling cracking reactor in an ethyl acrylate plant.

| | |
|---|---|
| Acrylic acid; | 15 wt % |
| Acrylic acid dimmer; | 7 wt % |
| Ethyl acrylate; | 3 wt % |
| Ethoxypropionic acid; | 36 wt % |
| Ethyl ethoxypropionate; | 13 wt % |
| Others (polymers, polymerization inhibitor, etc.); | 25.4 wt % |
| Water; | 0.6 wt % |

The high-boiling matter 1 and high-boiling matter 2 were mixed at ordinary temperature in ratios of 10:90, 50:50, and 90:10 by weight. After the mixing, the liquid state of each resultant mixture was examined. As a result, no precipitate was observed in each case. This Example 1 shows the state of mixtures of the high-boiling matter 1, in which the content of acrylic acid and its dimer is 80% by weight, and the high-boiling matter 2, in which the content thereof is 22% by weight. It can be seen that no change in liquid state occurs upon mixing because these high-boiling matters each are a hydrophilic high-boiling matter.

Example 2

Into the high-boiling-matter tank T shown in FIG. 5 were introduced the high-boiling matter 1 and the high-boiling matter 2 in a ratio of 10:4 by weight. The resultant mixture of both was satisfactory, and no precipitate was observed on the strainer of the pump used for circulating the tank liquid.

Comparative Example 1

A high-boiling matter 3 having the following composition was obtained from a high-boiling cracking reactor in a butyl acrylate plant.

| | |
|---|---|
| Acrylic acid; | 7 wt % |
| Acrylic acid dimmer; | 0 wt % |
| Butyl butoxypropionate; | 68 wt % |
| Butyl acrylate; | 11 wt % |
| Others (polymers, polymerization inhibitor, etc.); | 14 wt % |
| Water; | ≦0.1 wt % |

The high-boiling matter 1 and high-boiling matter 3 were mixed at ordinary temperature in ratios of 10:90, 50:50, and 90:10 by weight. In each case, a pasty polymer deposit was observed on the inner surface of the mixing vessel immediately after the mixing. The liquid state thereafter was examined and, as a result, the generation of a suspended solid matter was observed. This Comparative Example 1 shows the state of mixtures of the hydrophilic high-boiling matter 1, in which the content of acrylic acid and its dimer is 80% by weight, and the hydrophobic high-boiling matter 3, in which the content thereof is 7% by weight. This Comparative Example demonstrates that mixingthe high-boiling matters differing in liquid nature resulted in polymer precipitation.

Example 3

A high-boiling matter 4 having the following composition was obtained from a high-boiling cracking reactor in a 2-ethylhexyl acrylate plant.

| | |
|---|---|
| Acrylic acid; | 0.2 wt % |
| Acrylic acid dimmer; | 0 wt % |
| 2-Ethylhexyl 2-ethylhexoxypropionate; | 24 wt % |
| 2-Ethylhexyl acrylate; | 31 wt % |
| Others (polymers, polymerization inhibitor, etc.); | 44 wt % |
| Water; | ≦0.1 wt % |

The high-boiling matter 3 used in Comparative Example 1 and the high-boiling matter 4 were mixed at ordinary temperature in ratios of 10:90, 50:50, and 90:10 by weight. After the mixing, the liquid state of each resultant mixture was examined. As a result, no precipitate was observed in each case. This Example 3 shows the state of mixtures of the high-boiling matter 3, in which the content of acrylic acid and its dimer is 7% by weight, and the high-boiling matter 4, in which the content thereof is 0.2% by weight. It can be seen that no change in liquid state occurs upon mixing because these high-boiling matters each are a hydrophobic high-boiling matter.

Example 4

Into the high-boiling-matter tank T shown in FIG. 5 were introduced the high-boiling matter 3 and the high-boiling matter 4 in a ratio of 2:1 by weight. The resultant mixture of both was satisfactory, and no precipitate was observed on the strainer of the pump used for circulating the tank liquid.

Comparative Example 2

The high-boiling matter 1 and high-boiling matter 4 were mixed at ordinary temperature in ratios of 10:90, 50:50, and 90:10 by weight. In each case, a pasty polymer deposit was observed on the inner surface of the mixing vessel immediately after the mixing. The liquid state thereafter was examined and, as a result, the generation of a suspended solid matter was observed. This Comparative Example 2 shows the state of mixtures of the hydrophilic high-boiling matter 1, in which the content of acrylic acid and its dimer is 80% by weight, and the hydrophobic high-boiling matter 4, in which the content thereof is 0.2% by weight. This Comparative Example demonstrates that mixing the high-boiling matters differing in liquid nature resulted in polymer precipitation.

Comparative Example 3

The high-boiling matter 2 and high-boiling matter 3 were mixed at ordinary temperature in ratios of 10:90, 50:50, and 90:10 by weight. In each case, a pasty polymer deposit was observed on the inner surface of the mixing vessel immediately after the mixing. The liquid state thereafter was examined and, as a result, the generation of a suspended solid matter was observed. This Comparative Example 3 shows the state of mixtures of the hydrophilic high-boiling matter 2, in which the content of acrylic acid and its dimer is 22% by weight, and the hydrophobic high-boiling matter 3, in which the content thereof is 7% by weight. This Comparative Example demonstrates that mixing the high-boiling matters differing in liquid nature resulted in polymer precipitation.

Comparative Example 4

The high-boiling matter 2 and high-boiling matter 4 were mixed at ordinary temperature in ratios of 10:90, 50:50, and 90:10 by weight. In each case, a pasty polymer deposit was observed on the inner surface of the mixing vessel immediately after the mixing. The liquid state thereafter was examined and, as a result, the generation of a suspended solid matter was observed. This Comparative Example 4 shows the state of mixtures of the hydrophilic high-boiling matter 2, in which the content of acrylic acid and its dimer is 22% by weight, and the hydrophobic high-boiling matter 4, in which the content thereof is 0.2% by weight. This Comparative Example demonstrates that mixing the high-boiling matters differing in liquid nature resulted in polymer precipitation.

While the invention has been described in detail and with reference to specific embodiments thereof, it will be apparent to one skilled in the art that various changes and modifications can be made therein without departing from the spirit and scope thereof.

This application is based on a Japanese patent application filed on Nov. 20, 2001 (Application No. 2001-354043), the contents thereof being herein incorporated by reference.

INDUSTRIAL APPLICABILITY

According to the invention, even when high-boiling matters which have been discharged from a plant for producing (meth)acrylic acid and/or an ester thereof and are alike in liquid nature are mixed with each other in the same tank, no polymer precipitation occurs. The handling and storage thereof are hence easy. Consequently, tanks can be united into one, and the process is extremely advantageous in reducing the construction cost and the area necessary for equipment.

The invention claimed is:

1. A process for producing acrylic acid or methacrylic acid or an ester of any of these (hereinafter referred to as "(meth)acrylic acid compound") which is a process for producing and/or purifying a (meth)acrylic acid compound, characterized in that mixtures of high-boiling heavy ingredients (hereinafter referred to as "high-boiling matter mixtures") discharged from individual step units are classified by the content therein of acrylic acid or methacrylic acid (hereinafter referred to as "(meth)acrylic acid") and/or of the dimer thereof and handled, wherein the high-boiling matters are classified into a hydrophilic high-boiling matter in which the total content of (meth)acrylic acid and its dimer is 10% by weight or higher and a hydrophobic high-boiling matter in which the total content of the same is lower than 10% by weight, and handled.

2. A process for producing a (meth)acrylic acid compound selected from the group consisting of an acrylic acid, a methacrylic acid, an ester of an acrylic acid and an ester of a methacrylic acid, comprising:

at least one of producing and purifying the (meth)acrylic acid compound in one or more individual step units, wherein the producing, the purifying, or both the producing and the purifying, forms at least three mixtures of high-boiling components, including at least one hydrophilic high-boiling mixture having a total content of (meth)acrylic acid and the dimer of (meth)acrylic acid of 10% by weight or greater, and at least two different hydrophobic high-boiling mixtures having a total content of (meth)acrylic acid and the dimer of (meth)acrylic acid of less than 10% by weight; and treating the hydrophilic high-boiling mixture;

mixing the two different hydrophobic high boiling mixtures to form a storage mixture consisting of the hydrophobic high boiling mixtures, and storing the storage mixture at ambient temperature without precipitation of a polymer;

wherein % by weight is based on the total weight of the mixture.

3. The process as claimed in claim 2, wherein the individual step units are selected from the group consisting of a separating unit, a concentrating unit, a recovering unit, and a purifying unit.

4. The process as claimed in claim 2, wherein one or more of the hydrophilic and hydrophobic high-boiling mixtures is obtained from a residue of a distillation column for separating (meth)acrylic acid.

5. The process as claimed in claim 2, wherein at least one of the hydrophobic high-boiling mixtures is a residue from a cracking reactor for the (meth)acrylic acid compound.

6. The process as claimed in claim 2, wherein at least one of the hydrophobic high-boiling mixtures has a water content of 2% by weight or lower.

7. The process as claimed in claim 2, further comprising:
mixing and storing two or more hydrophilic high-boiling mixtures in the same storage tank.

8. The process as claimed in claim 2, wherein the at least two different hydrophobic high-boiling mixtures each have a total content of (meth)acrylic acid and the dimer of (meth)acrylic acid of less than 8% by weight.

* * * * *